United States Patent [19]

Ikegawa et al.

[11] Patent Number: 5,097,042

[45] Date of Patent: Mar. 17, 1992

[54] WATER-SOLUBLE BENZIMIDAZOLOTRIAZOLE DERIVATIVE OR SALT THEREOF

[75] Inventors: Akihiko Ikegawa; Junji Nishigaki, both of Kanagawa, Japan

[73] Assignee: Fuji Photo Film Co., Ltd., Kanagawa, Japan

[21] Appl. No.: 607,326

[22] Filed: Oct. 30, 1990

[30] Foreign Application Priority Data

Nov. 2, 1989 [JP] Japan .................. 1-286659

[51] Int. Cl.$^5$ .......................... C07D 249/16
[52] U.S. Cl. ................................. 548/262.4
[58] Field of Search ...................... 548/262.4

[56] References Cited

PUBLICATIONS

Tyurenkova et al., "Synthesis and Some Reactions, etc.", CA 62: 16234e (1965).

*Primary Examiner*—Patricia L. Morris

*Attorney, Agent, or Firm*—Sughrue, Mion, Zinn, Macpeak & Seas

[57] ABSTRACT

A water-soluble benzimidazolotriazole derivative of formula (I):

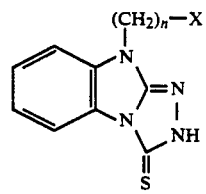

wherein X represents a sulfo group, a sulfonato group or a $-N-(R)_2$ group, R represents an alkyl group having 6 carbon atoms or less; and n represents a natural number of 8 or less. The benzimidazolotriazole derivative of formula (I) may form a salt with an organic or inorganic acid.

8 Claims, No Drawings

WATER-SOLUBLE BENZIMIDAZOLOTRIAZOLE DERIVATIVE OR SALT THEREOF

FIELD OF THE INVENTION

This invention relates to a water-soluble benzimidazolotriazole derivative which is of great use in a variety of chemical fields such as photochemistry, pharmaceuticals and agricultural chemicals.

BACKGROUND OF THE INVENTION

A variety of benzimidazolotriazole derivatives are known such as the compounds described in U.S. Pat. Nos. 3,137,574 and 2,887,378; British Patent 851,816; *J. Org. Chem.* (Journal of Organic Chemistry), Vol. 24, p. 1478-1486 (1959); JP-B49-11063 (the term "JP-B" as used herein means an "examined Japanese patent publication"); *J. Heterocyclic Chem.* (Journal of Heterocyclic Chemistry), Vol. 15, p. 1027-1031 (1978); and *J. Org. Chem.* (Journal of Organic Chemistry), Vol. 38, p. 3084-3086 (1973). However, previously disclosed compounds are all of low in solubility in aqueous solvents which made them inconvenient to use for most practical applications.

SUMMARY OF THE INVENTION

An object of the invention is to provide a novel benzimidazolotriazole derivative.

Another object of the invention is to provide a benzimidazolotriazole derivative having high watersolubility.

These and other objects of the invention have been realized by a water-soluble benzimidazolotriazole derivative of formula (I) or a salt thereof.

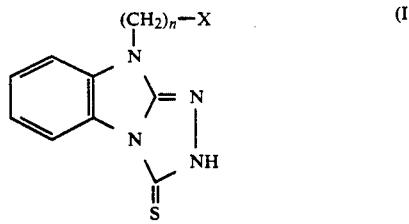

In formula (I) X represents a sulfo group, a sulfonato group or a —N—(R)$_2$ group, R represents an alkyl group having 6 carbon atoms or less, preferably 1 to 4 carbon atoms; and n represents a natural number of 8 or less, preferably 2 to 6.

DETAILED DESCRIPTION OF THE INVENTION

Some specific examples of the alkyl group represented by R in the formula (I) are a methyl, an ethyl, a propyl, an isopropyl, a butyl, a sec-butyl, a tert-butyl, a pentyl, an isopentyl, a hexyl, and a cyclohexyl group. Most preferably R represents a methyl, an ethyl, an isopropyl, or a butyl group.

The derivative represented by formula (I) may also form a salt with an organic or inorganic acid. Some examples of such organic or inorganic acids include hydrochloric acid, sulfuric acid, hydrobromic acid, hydroiodic acid, hydrofluoric acid, oxalic acid, p-toluenesulfonic acid, and naphthalenedisulfonic acid.

Further, the compound represented by the formula (I) can take an enol type structure through tautomerism as shown below:

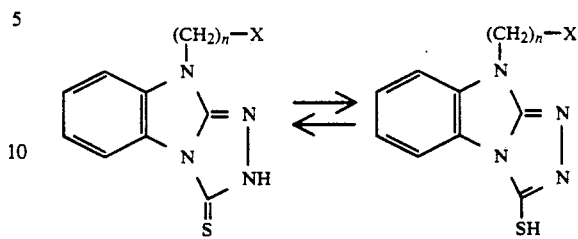

Specific compounds of the present invention are shown in the following Examples but these do not limit the scope of the invention.

Unless otherwise indicated all ratios and percentages are by weight.

TABLE 1

| No. | X | n | m.p. (°C.) |
|---|---|---|---|
| 1 | (C$_2$H$_5$)$_2$N— · HCl | 2 | 258-260 |
| 2 | (CH$_3$)$_2$N— · HCl | 2 | 251-253 |
| 3 | (C$_2$H$_5$)$_2$N— · HCl | 3 | 256-257 |
| 4 | (C$_4$H$_9$)$_2$N— · HCl | 2 | 183-185 |
| 5 | (CH$_3$)$_2$N— · HCl | 6 | 275-278 |
| 6 | NaO$_3$S— | 3 | >300 |

EXAMPLES

Synthesis of Compound 1

A suspension of 164 g (1.0 mol) of 2-methylthiobenzimidazole (manufactured by Tokyo Kasei Co. or Aldrich Co.) in 1500 ml of water was prepared. To it were added 1.65 g (0.005 mol) of sodium tungstate dihydrate and 280 ml of 35% aqueous hydrogen peroxide. The mixture was placed in a water bath of 50° C. and stirred for 6 hours. During this period, 181 g of 2-methanesulfonylbenzimidazole precipitated and was collected by filtration.

A mixture of 70 g (0.36 mol) of 2-methanesulfonylbenzimidazole, 74 g (0.4 mol) of 1-chloro-2-diethylaminoethane hydrochloride, and 119 ml of triethylamine was heated under reflux in 700 ml of acetonitrile for 3 hours.

The triethylamine hydrochloride precipitated was separated by filtration. The filtrate was concentrated under reduced pressure and then extracted with ethyl acetate (1000 ml×2). The ethyl acetate layer was dried over magnesium sulfate and then concentrated under reduced pressure to yield 85.3 g of 1-(2-diethylaminoethyl)-2-methanesulfonylbenzimidazole as crystals.

85 g of 1-(2-diethylaminoethyl)-2-methane-sulfonyl-benzimidazole was heated under reflux for 4 hours in 200 ml of hydrazine monohydrate. The product of this reaction was extracted with ethyl acetate and dried over Glauber's salt. A syrup residue was obtained by drying under reduced pressure. To this residue were added isopropanol and 20 ml of hydrochloric acid to yield 84 g of 1-(2-diethylaminoethyl)-2-hydrazinobenzimidazole dihydrochloride as crystals.

The 84 g of 1-(2-diethylaminoethyl)-2-hydrazinobenzimidazole dihydrochloride was suspended in acetonitrile. To this suspension were added 19 ml of carbon disulfide and 80 ml of triethylamine, and the mixture was stirred at 60° C., whereby a complete solution was obtained. Stirring was continued at 60° C. for 2 hours and the solution was ice-cooled to precipitate crystals. These crystals were collected by filtration, then suspended in 500 ml of methanol and completely dissolved by adding 20 ml of hydrochloric acid. The solution was again ice-cooled to precipitate crystals, which were collected by filtration to yield 40 g of 8(2-diethylaminoethyl)-3-mercaptobenzimidazolotriazole (Compound 1) having the following characteristics:

m.p. 258°-260° C.

Elemental analysis:

Calcd.: C:54.58; H:5.29; N:17.14; S:11.21;

Found : C:54.60; H:5.25; N:17.01; S:11.30;

Other derivatives are synthesized according to this method as shown in Table 1.

The solubility of Comparative Compound (A) was compared with the solubility of embodiments of the invention in distilled water and a fixing solution for photography (Fuji F manufactured by Fuji Photo Film Co., Ltd.). The results of this comparison are shown in Table 2 below.

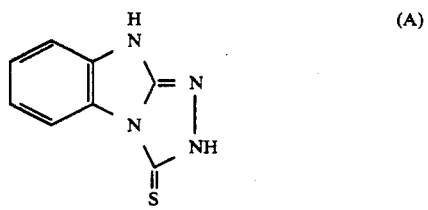

(A)

Compound (A) is described in *J. Orq. Chem.*, 24, 1478 (1959)

TABLE 2

| Compound | Amount Added | Distilled Water 1 liter (25° C.) | Fuji F 1 liter (25° C.) |
|---|---|---|---|
| A (Comp. Ex.) | 2 g | Insoluble | Insoluble |
| 1 (Invention) | " | Soluble | Soluble |
| 2 (Invention) | " | " | " |
| 3 (Invention) | " | " | " |
| 4 (Invention) | " | " | " |
| 5 (Invention) | " | " | " |

TABLE 2-continued

| Compound | Amount Added | Distilled Water 1 liter (25° C.) | Fuji F 1 liter (25° C.) |
|---|---|---|---|
| 6 (Invention) | " | " | " |

As shown in Table 2, the compounds of the present invention are highly soluble in aqueous solvents, particularly in an aqueous solution with high salt concentration such as fixing solution for photography.

The benzimidazolotriazole derivative of the present invention or its salt has higher watersolubility compared to previously known benzimidazolotriazole derivatives. This makes the compounds of the invention particularly useful in such fields as photochemistry, pharmaceuticals, and agricultural chemicals.

While the invention has been described in detail and with reference to specific embodiments thereof, it will be apparent to one skilled in the art that various changes and modifications can be made therein without departing from the spirit and scope thereof.

What is claimed is:

1. A water-soluble benzimidazolotriazole derivative of formula (I):

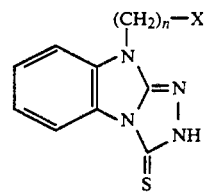

wherein X represents a sulfo group, a sulfonato group or a —N—(R)$_2$ group, R represents an alkyl group having 6 carbon atoms or less; and n represents a natural number of 8 or less.

2. A water-soluble benzimidazolotriazole derivative as claimed in claim 1, wherein R is a methyl group, an ethyl group, a propyl group, an isopropyl group, a butyl group, a sec-butyl group, a tert-butyl group, a pentyl group, an isopentyl group, a hexyl group, or a cyclohexyl group.

3. A water-soluble benzimidazolotriazole derivative as claimed in claim 1, wherein R is a methyl group, an ethyl group, an isopropyl group, or a butyl group.

4. A water-soluble benzimidazolotrizole derivative as claimed in claim 1, wherein X is NaO$_3$S—.

5. A water-soluble benzimidazolotriazole derivative as claimed in claim 1, wherein the derivative of formula (I) forms a salt with an organic or inorganic acid selected from the group consisting of hydrochloric acid, sulfuric acid, hydrobromic acid, hydroiodic acid, hydrofluoric acid, oxalic acid, p-toluenesulfonic acid and naphthalenedisulfonic acid.

6. A water-soluble benzimidazolotriazole derivative as claimed in claim 5, wherein R is a methyl group, an ethyl group, a propyl group, an isopropyl group, a butyl group, a sec-butyl group, a tert-butyl group, a pentyl group, an isopentyl group, a hexyl group, or a cyclohexyl group.

7. A water-soluble benzimidazolotriazole derivative as claimed in claim 5, wherein R is a methyl group, an ethyl group, an isopropyl group, or a butyl group.

8. A water-soluble benzimidazolotriazole derivative as claimed in claim 5, wherein X is HCl·(CH$_3$)$_2$N—, HCl·(C$_2$H$_5$)$_2$N—, or HCl·(C$_4$H$_9$)$_2$N—.

* * * * *